(12) United States Patent
Kanner et al.

(10) Patent No.: US 12,121,683 B2
(45) Date of Patent: *Oct. 22, 2024

(54) ADVANCED ACTUATING MECHANISM AND METHOD OF OPERATION FOR FLUID DISPLACEMENT AND PRESSURIZING DEVICE

(71) Applicant: Atrion Medical Products, Inc., Arab, AL (US)

(72) Inventors: Rowland W. Kanner, Guntersville, AL (US); Jonathan Collins, Arab, AL (US); Emma Catherine Shirley, Easley, SC (US)

(73) Assignee: Atrion Medical Products, Inc., Arab, AL (US)

( * ) Notice: Subject to any disclaimer, the term of this patent is extended or adjusted under 35 U.S.C. 154(b) by 101 days.

This patent is subject to a terminal disclaimer.

(21) Appl. No.: 17/965,476

(22) Filed: Oct. 13, 2022

(65) Prior Publication Data

US 2023/0122534 A1  Apr. 20, 2023

Related U.S. Application Data

(60) Provisional application No. 63/256,311, filed on Oct. 15, 2021.

(51) Int. Cl.
| | |
|---|---|
| *A61M 25/10* | (2013.01) |
| *A61F 2/95* | (2013.01) |
| *A61F 2/958* | (2013.01) |
| *F04B 35/01* | (2006.01) |

(52) U.S. Cl.
CPC ..... *A61M 25/10182* (2013.11); *A61F 2/9517* (2020.05); *A61F 2/958* (2013.01); *F04B 35/01* (2013.01)

(58) Field of Classification Search
CPC . A61M 25/10182; A61F 2/9517; A61F 2/958; F04B 35/01; F04B 13/00; F04B 53/06; F04B 9/14
See application file for complete search history.

(56) References Cited

U.S. PATENT DOCUMENTS

| | | |
|---|---|---|
| 3,749,084 A | 7/1973 | Cucchiara |
| 4,476,866 A | 10/1984 | Chin |
| 4,583,978 A | 4/1986 | Porat et al. |
| 4,702,737 A | 10/1987 | Pizzino |
| 4,758,223 A | 7/1988 | Rydell |
| 5,392,790 A | 2/1995 | Kanner |

(Continued)

*Primary Examiner* — Brian A Dukert
*Assistant Examiner* — Rebecca Lynee Zimmerman
(74) *Attorney, Agent, or Firm* — Clark Hill PLC; James R. Foley

(57) ABSTRACT

A fluid displacement and pressurizing device which includes a housing, a first piston in the housing, a plunger which extends from the housing and has a second piston thereon, and an actuator that works to selectively lock the piston to either the housing or the plunger depending on the position of the second piston in the housing. Effectively, the actuator includes a first locking mechanism that locks and unlocks the first piston relative to the housing and a second locking mechanism that locks and unlocks the plunger relative to the piston. As such, the first locking mechanism is not only a locking mechanism but is also an actuating mechanism with regard to actuating the second locking mechanism.

21 Claims, 12 Drawing Sheets

(56) References Cited

U.S. PATENT DOCUMENTS

| | | | |
|---|---|---|---|
| 5,512,054 A * | 4/1996 | Morningstar | A61M 5/31511 604/218 |
| 6,190,354 B1 | 2/2001 | Sell | |
| 9,265,919 B2 | 2/2016 | Kanner | |
| 9,452,279 B2 | 9/2016 | Stevens et al. | |
| 10,238,843 B2 | 3/2019 | Stevens et al. | |
| 2002/0133116 A1 | 9/2002 | Davis | |
| 2012/0067204 A1 | 3/2012 | Kanner | |
| 2016/0235458 A1 | 8/2016 | Roberts | |
| 2017/0000988 A1 * | 1/2017 | Stevens | A61M 25/10182 |
| 2021/0085952 A1 | 3/2021 | Saar et al. | |

* cited by examiner

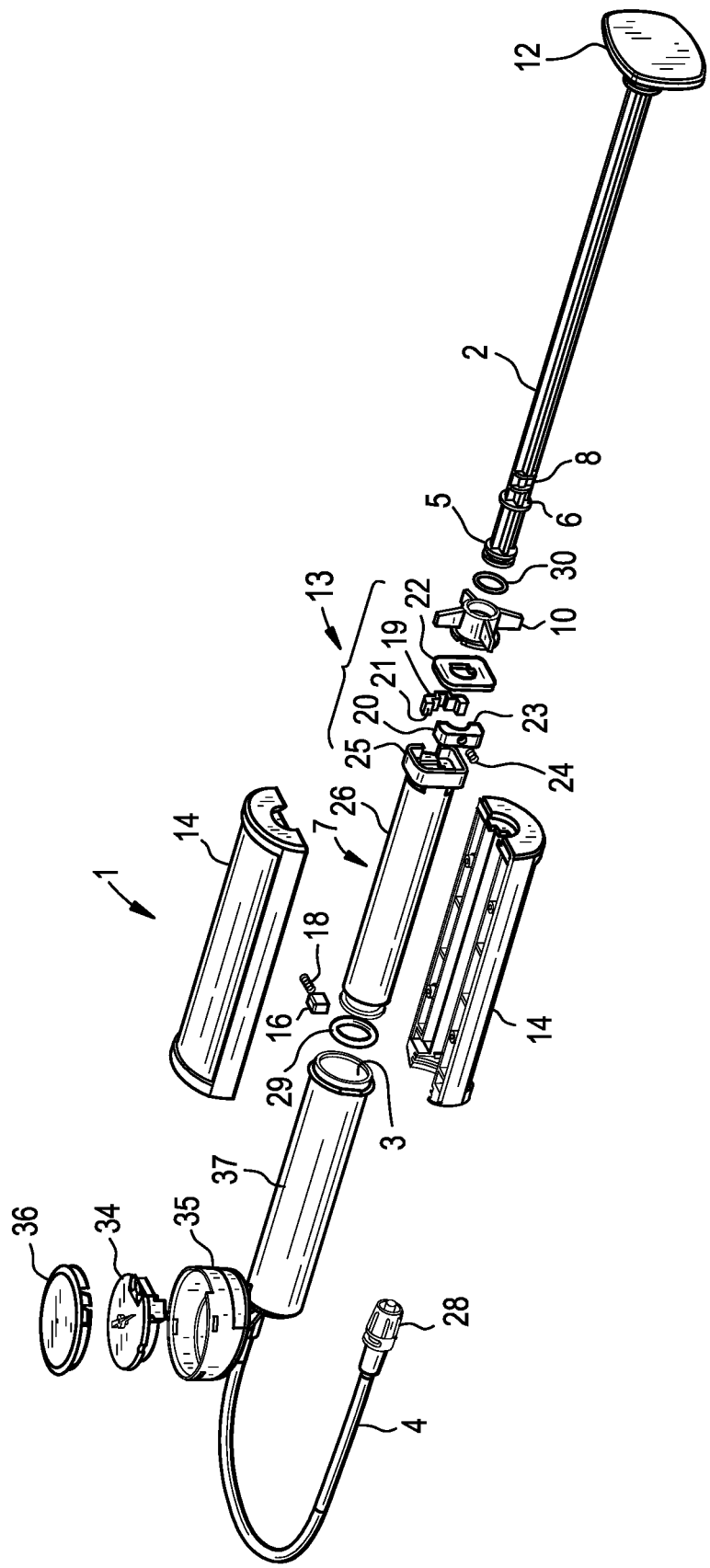

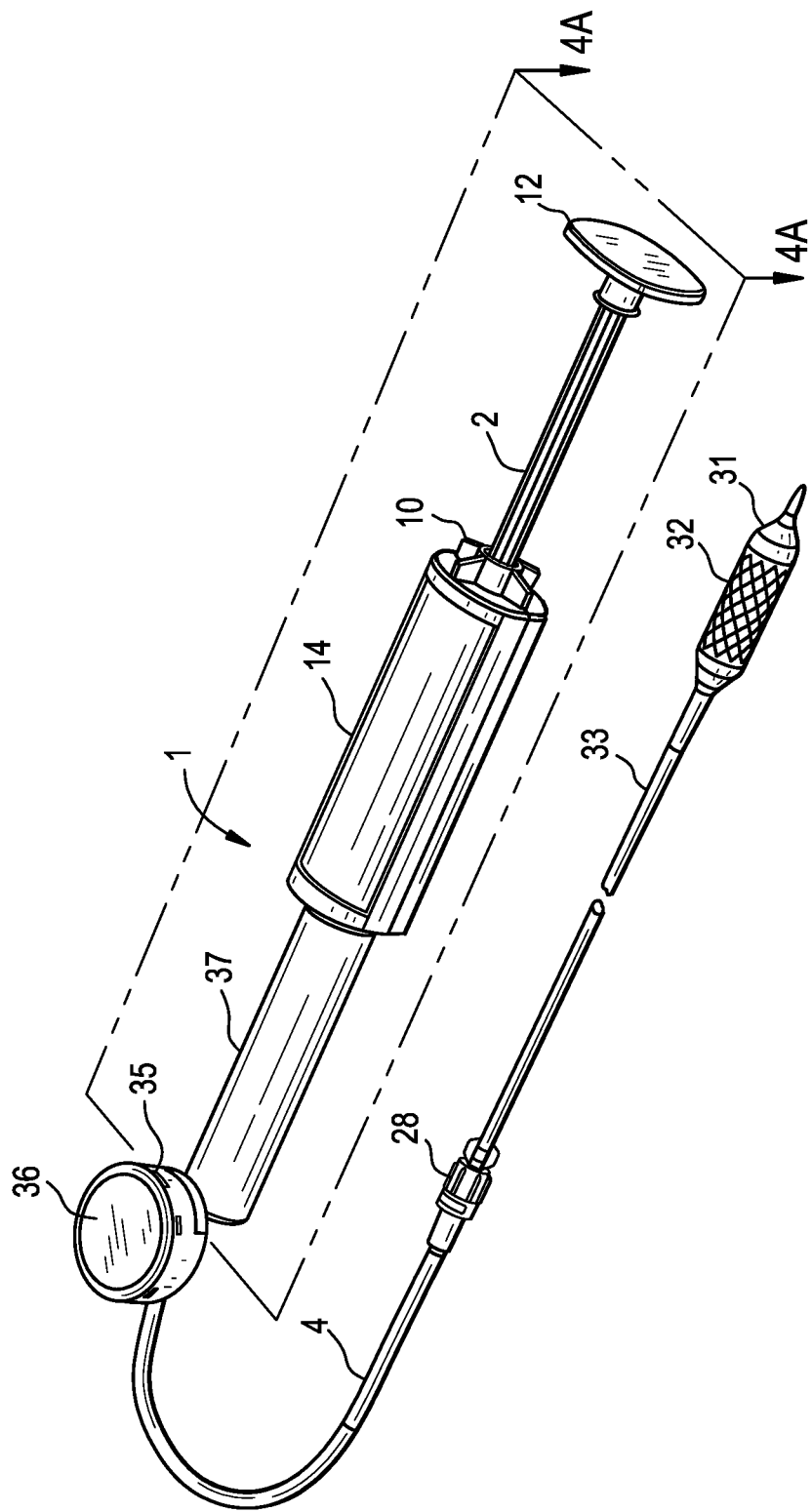

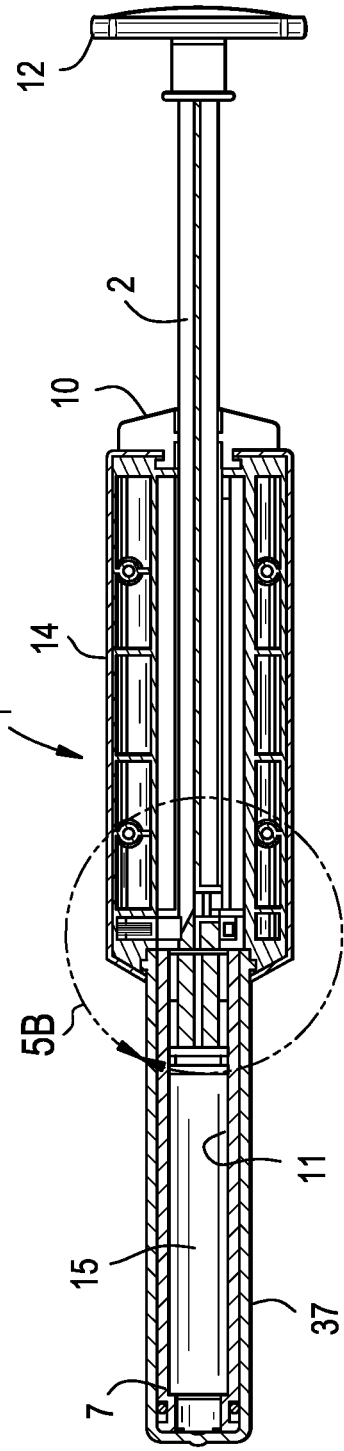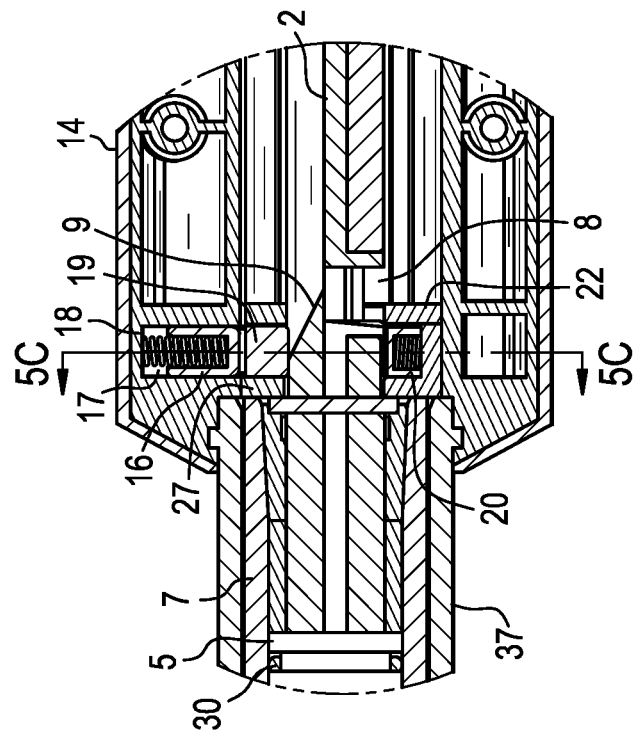

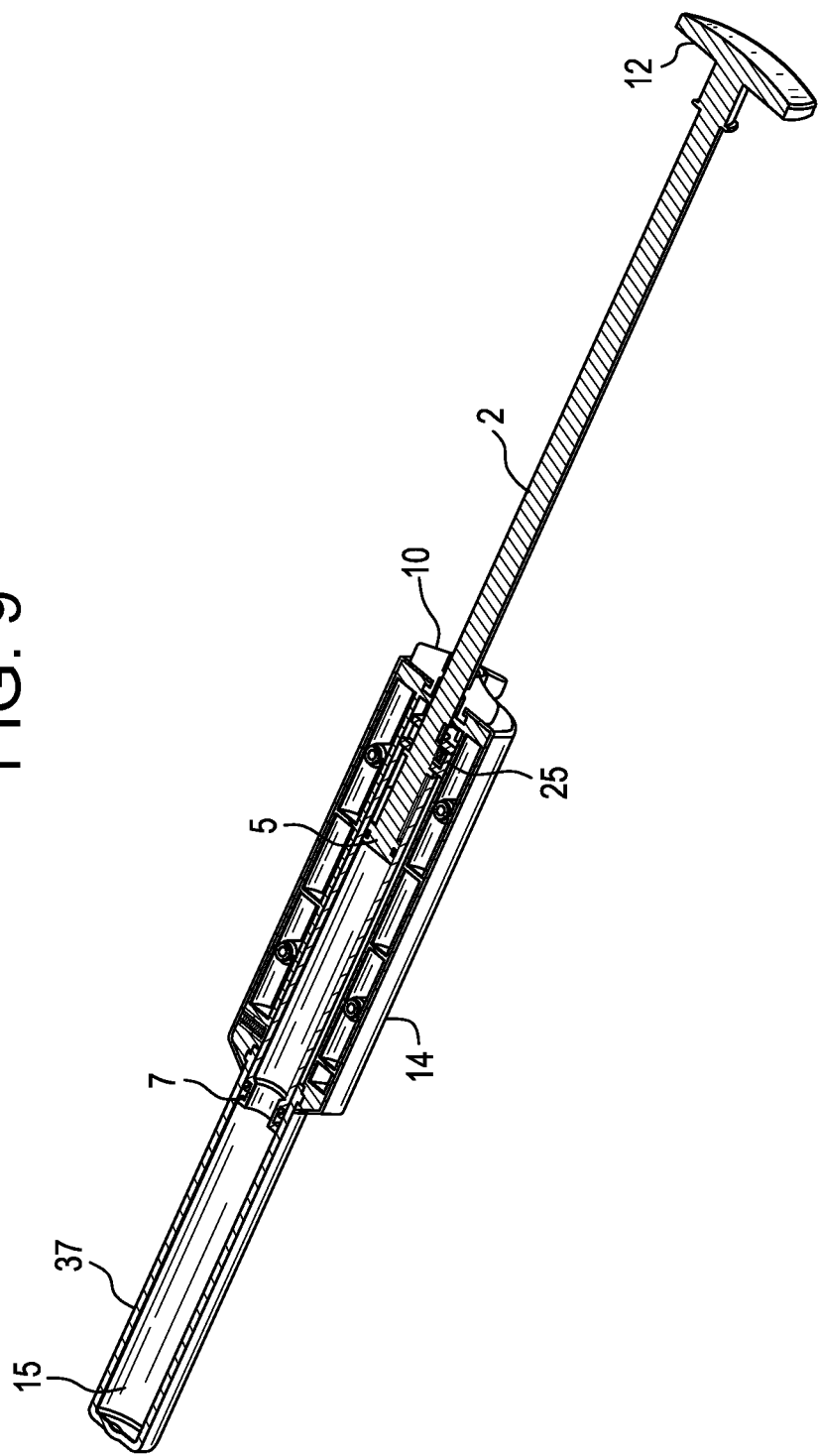

ADVANCED ACTUATING MECHANISM AND METHOD OF OPERATION FOR FLUID DISPLACEMENT AND PRESSURIZING DEVICE

BACKGROUND

The present invention generally relates to a fluid pressurizing mechanism and method for expanding and deflating catheter balloons or the like, and more specifically relates to a device having a plunger actuating mechanism that is very intuitive, easy to use and seamless in operation.

Fluid pressurization devices are used for selectively delivering and relieving a measured volume of fluid under high pressure for balloon angioplasty and stent delivery procedures interiorly of blood vessels as well as other types of balloon catheter driven procedures including treatment of aortic aneurism and heart valve delivery. Large piston, high volume fluid delivery devices for this purpose often rely upon a plunger screw and nut mechanism to provide the necessary mechanical advantage for creating elevated pressures. Due to their typically large piston diameter, a common 40 mL displacement device, for example, could require a plunger force loading of 92 lb F (41.7 Kg F) to expand an 8 atm (117.6 psi) high-capacity balloon. In some procedures requiring high volume displacement, expansion of the catheter's balloon must be accomplished more quickly than possible using the plunger screw mechanism. Examples of such procedures include balloon expansion of an endovascular stent graft to treat an abdominal aortic aneurism (AAA) or placement and expansion of an aortic valve in a transcatheter (TAVR) procedure. During these procedures, expansion of the catheter's balloon used to deliver such expandable prosthetic devices completely obstructs essential circulatory blood flow within the body. In these instances, it is desirable to minimize the time duration of blood flow obstruction during balloon expansion to a small number of seconds. Under these use conditions, there is simply not enough time for a clinician to rotate the plunger screw mechanism in order to achieve the pressure level required by the delivery balloon. Additionally, since some of these procedures must limit stent expansion to a desired balloon diameter in order to avoid distorting the stent or a heart valve during delivery, delivered fluid volume and not pressure therefore becomes the necessary delivery control factor. In these instances, an exact predetermined amount of working fluid must be loaded into the inflation device and subsequently delivered in its entirety to the catheter balloon by fully displacing all working fluid within the device during balloon expansion. A very specialized inflation device is therefore required for these procedures.

A previously improved inflation device to achieve full pressure balloon expansion involves use of a smaller diameter piston, one that will allow the clinician to reach 8 atm of pressure for instance, through straight manual application of plunger force in the range of 50-52 lb F (22.7-23.6 Kg F). Balloon inflation devices of this type are often used because they allow the clinician to quickly and completely discharge the contents of the inflation device into the stent delivery balloon through continuous manual compression of the plunger without reliance upon the plunger screw and nut mechanism. In order to achieve the fluid volume capacity demanded with this smaller piston approach, a longer plunger stroke and therefore a much longer bore becomes necessary compared to the large piston device. In practice, manufacturing such a long, small diameter bore within the device barrel has proven to be challenging for the resin molding process typically used for production of these disposable devices. This resin molding challenge is further made difficult by the need to produce a device bore with little or no draft (bore taper to assist the part molding process) in order to assure reliability of the piston's seal during use.

It has been recognized that although more attainable plunger forces in the range of 50-52 lb F allow rapid expansion of large balloons to full pressure, even this amount of force is beyond the ability of some clinicians who must therefore resort to achieving final pressurization of the catheter balloon by using the inflation device's plunger screw and nut mechanism. This extra step to achieve full fluid delivery and balloon expansion dramatically hinders prosthetic device placement times for procedures that should be accomplished in only a small number of seconds. Unfortunately, although the ergonomic benefit of yet a smaller piston and bore could further reduce user input force, the device's suitability for manufacturing would suffer greatly due to practical limitations of the molding process required to make it. Addition of a small secondary piston could be possible however, manually switching between a pair of pistons can be unnecessarily confusing and cumbersome to a user whose past training and experience has involved the simplicity of applying a continuous force upon a single plunger to accomplish a syringe-like task.

Examples of prior art multiple piston single barrel syringe designs include the devices disclosed in U.S. Pat. Nos. 3,749,084, 4,583,978 and 4,702,737. All three of these patents disclose multiple dose syringes having more than one piston to deliver multiple individual fractional doses from a single, larger medicament filling.

U.S. Pat. No. 4,476,866 discloses a dual piston syringe designed to operate in a manner in which the smaller internal piston is first advanced to create a preliminary high-pressure condition to initiate an inversion movement of a balloon before being filled at lower pressure by moving the larger piston after the smaller piston's plunger thumb button bottoms upon it.

U.S. Pat. No. 4,758,223 discloses a syringe barrel having dual coaxially arranged bores that contain a user selectable dual piston plunger arrangement such that the large piston and the small piston are independently operable within their respective syringe barrel bores.

United States Application Publication No. US2021/0085952 A1 discloses a dual piston inflation device having a main piston assembly bearing a one-way valve and containing an axially arranged inner bore, the inner bore being made to receive an operable plunger bearing the second smaller piston. In operation, once this device has been charged with working fluid, pressing against the small piston plunger should first drive the large piston distally to deliver its working fluid to a balloon, provided that the valve within the large piston has sufficient resistance to opening in response to building pressure between it and the small piston. Once the large piston encounters the "opening protrusion" feature mounted distally within the larger piston's barrel, which is designed to open the valve, fluid under pressure created by the small piston can then be delivered out a central lumen of the valve opening feature. This design is quite similar conceptually, and in operating principal, with the dual dose syringe disclosed in U.S. Pat. No. 4,702,737, and previously cited above.

U.S. Pat. Nos. 9,452,279 and 10,238,843 disclose a very complex multiple piston syringe design having three coaxial pistons within. The intent of this device is to provide a reduction in the user force required to deliver higher pressures with a small piston following displacement of a greater volume of fluid to a certain pressure that is lower than that which the small piston alone is capable of delivering. In operation, the greater volume is allowed to be displaced by proximal movement of all three pistons together, until a triggering pressure is reached within the fluid chamber. Upon reaching that triggering pressure, the largest piston is caused to displace proximally relative to the advanced plunger handle and trigger a chain of events that both locks the intermediate piston into locked engagement with the housing and releases the small piston to be advanced distally alone. This shift occurs either: a) upon reaching a certain fluid chamber pressure; or b) upon being driven with sufficient force by the operator against the end of the syringe bore if the triggering pressure had not yet been reached. One must also recognize that the pressure at which this shift occurs in either scenario, is strictly controlled by the stiffness of flexible polymer fingers engaged into mating plunger stops and the friction that must be overcome in order to dislodge these fingers from their mating plunger stops. The variability inherent with such a mechanism makes it unsuitable for use in delivering those stents that require size control solely through precise fluid volume delivery instead of pressure. The fact that functioning of this device depends upon pressure, challenges its suitability for applications that demand total delivery of a precisely set fluid volume.

Although several prior art devices exist, there is a need for an advanced balloon catheter inflation device that requires less user input force during rapid large balloon stent delivery procedures.

SUMMARY

An object of an embodiment of the present invention is to provide an advanced balloon catheter inflation device that requires less user input force.

Another object of an embodiment of the present invention is to provide an advanced balloon catheter inflation device that is configured such that operation of the device simply requires the user to rapidly drive its plunger distally inward to displace the working fluid into the catheter balloon and after reaching complete fill, withdraw the plunger fully to exhaust the delivered fluid and collapse the balloon.

Another object of an embodiment of the present invention is to provide an advanced balloon catheter inflation device that reduces the required end of fill user input delivery force.

Yet another object of an embodiment of the present invention is to provide an advanced balloon catheter inflation device that is configured to assure that procedures can be accomplished without having to resort to the assistance of a threaded plunger.

Still yet another object of an embodiment of the present invention is to provide an advanced balloon catheter inflation device that does not require an extremely long and smaller bore in order to achieve a reduction in user input force to deliver an identical fluid volume.

Yet still another object of an embodiment of the present invention is to provide an advanced balloon catheter inflation device having piston bores that are fully open and unobstructed by valves or other air or fluid trapping features.

Briefly, an embodiment of the present invention provides a fluid displacement and pressurizing device which comprises a housing, a first piston in the housing, a plunger which extends from the housing and has a second piston thereon, and an actuator that works to selectively lock the first piston to either the housing or the plunger depending on the position of the second piston in the housing.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which:

FIG. 2 is an exploded perspective view of an advanced inflation device which is in accordance with an embodiment of the present invention;

FIG. 3 is a perspective view of the assembled advanced inflation device with delivery balloon catheter and expandable prosthetic device;

FIG. 5A is similar to FIG. 4A but shows a different state of the locking slide assembly, specifically a state during which the plunger is unlocked from the large piston.

FIG. 5B is an enlarged view of a portion of FIG. 5A;

FIG. 9 is similar to FIG. 4A but shows the plunger in the fully proximal, filled position.

DESCRIPTION OF AN ILLUSTRATED EMBODIMENT

Figure 1:
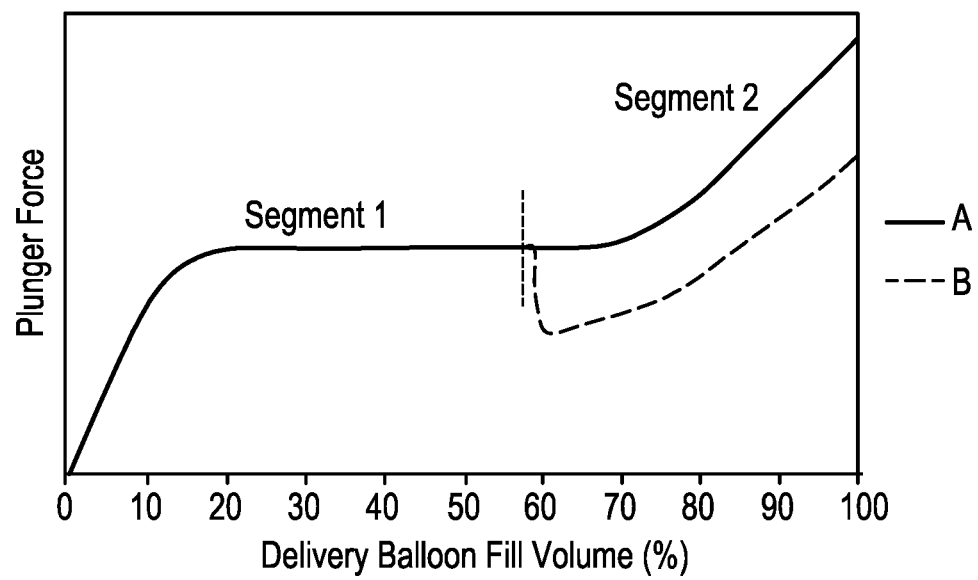
FIG. 1 is a graph showing plunger force vs. fluid volume delivered to catheter balloon.

While this invention may be susceptible to embodiment in different forms, there is shown in the drawings and will be described herein in detail, a specific embodiment with the understanding that the present disclosure is to be considered an exemplification of the principles of the invention, and is not intended to limit the invention to that as illustrated.

An advanced balloon catheter inflation device, one requiring even less user input force than the previously discussed improved inflation device during rapid large balloon stent delivery procedures, is disclosed herein. This approach effectively takes into consideration the non-linear way plunger force rises during balloon delivery of large expandable prosthetic devices with particular focus upon the high force requirements occurring at the end of balloon fill. As illustrated in the example of curve "A" in FIG. 1 shown for the previously improved single piston inflation device, a significant increase in plunger force rate begins when the balloon is between 50% and 80% filled, before the remaining 50% to 20% of inflation fluid has been delivered. Operation of the advanced balloon catheter inflation device disclosed herein simply requires the user to rapidly drive its plunger distally inward to displace the working fluid into the catheter balloon and after reaching complete fill, withdraw the plunger fully to exhaust the delivered fluid and collapse the balloon. This device has the ability to reduce the required end of fill user input delivery force of the previously discussed improved smaller piston device, from 50-52 lb F (22.7-23.6 Kg F) for example, to 30-32 lb F (13.6-14.5 Kg F) thereby allowing less robust practitioners to quickly and comfortably deliver an endovascular aortic stent graft or perform a TAVR procedure. Significantly, these procedures can be accomplished without need to resort to the assistance of a threaded plunger often required by other such devices. Additionally, significant from a manufacturing standpoint is the fact that this advanced device does not require an extremely long and smaller bore than the previously discussed improved device in order to achieve a reduction in user input force to deliver an identical fluid volume. In fact, in the instance of this advanced inflation device, the device can actually be made shorter for any given displacement. Further, the displacement ratio between its two pistons can also be adjusted to best match a desired plunger input force for a specific delivery balloon fill response. Finally, the advanced balloon catheter inflation device is designed with its piston bores fully open and unobstructed by valves or other air or fluid trapping features such as the annular dead volume surrounding the valve opening protrusion within the design shown in United States Application Publication No. US2021/0085952 A1, discussed above. Therefore, without the obstruction of a valve the advanced inflation device disclosed herein, can be easily and quickly purged of all air to assure accurate fill during preparation and accurate fluid delivery during balloon inflations.

FIG. 2 is an exploded perspective view of an advanced inflation device 1 which is in accordance with an embodiment of the present invention. FIG. 3 is a perspective view of the assembled device 1, showing the device 1 connected to a delivery balloon catheter 33 and expandable prosthetic device 32.

The device 1 comprises a housing 14 and a barrel 37 which extends from the housing 14. Parts 14 and 37 collectively form an overall housing of the device 1. However, for simplicity the term "housing" will be mainly used to refer to part 14 and the term "barrel" will be mainly used to refer to part 37.

A control plunger 2 extends out of the housing 14 and preferably there is a handle 12 on the end of the plunger 2. Preferably, a holding mechanism 10 is provided on the housing 14 for selectively locking and unlocking the plunger 2 in place relative to the housing 14. As shown in FIG. 3, the device 1 is configured such that a hose 4 is connectable to the device 1, such as proximate the end of the barrel 37. As shown, a Luer connector 28 may be provided at the end of the hose 4 for connection to a catheter 33, and the catheter 33 may include a delivery balloon 31 for engaging an expandable prosthetic device 32. The hose 4 is in communication with the fluid chamber 15 (identified in FIGS. 4A, 5A, 6B, 7A, 8 and 9) in the device 1 such that the device 1 can be used to inflate and deflate the delivery balloon 31.

Preferably, the device includes a pressure gauge which is in communication with the fluid chamber 15. The gauge is provided so a user can view the gauge and determine what pressure is being provided to the delivery balloon. The pressure gauge can be of the traditional screw in type of pressure sensing and display module or be provided as shown in FIG. 2 with an integral pressure sensing and display module housing 35, having a mechanical or electronic pressure sensing and display module 34 that is protected with a lens 36.

In operation, a user holds the housing 14 and then either pushes the handle 12 of the plunger 2 into/toward the housing 14 to increase the pressure and inflate the delivery balloon 31, or pulls the handle 12 of the plunger 2 out of/away from the housing 14 to decrease the pressure and deflate the delivery balloon 31. All functions of the device 1 are performed by simply moving the single control plunger 2 distally, or withdrawing it proximally, within a bore 3 (see FIG. 2) of the barrel 37.

As shown in FIG. 2, the plunger 2 may be provided without any threads along its length, and a small piston 5 is preferably provided at the end of the plunger 2, opposite the end that has the handle 12. This small piston 5 can be integrally formed with the plunger 2 or can be attached to the end of the plunger 2. Preferably, a piston seal 30 is provided on the small piston 5 for sealing with a bore 11 of a large piston 7 (the bore 11 is identified in FIG. 5A, and the seal can be seen in FIG. 5B). A piston seal 29 is also preferably provided on the large piston 7 for sealing with a bore 3 of the barrel 37 (see FIG. 6B). As such, the small piston 5 slides back and forth in the bore 11 of the large piston 7, and the large piston 7 slides back and forth in the bore 3 of the barrel 37, and both at all times provide a seal against their respective bores.

A locking slide assembly 13 is provided at the end of the large piston 7, preferably within a locking chamber 25 that is sealed by a locking chamber cover 22. The locking slide assembly 13 preferably comprises a plunger latch 20, a latch biasing member such as a compression spring 24, and an actuator block 19.

The piston 5 also preferably provides a piston shoulder 6 as well as at least one plunger stop 8, and there is a bolt 16 inside the housing 14 that is driven toward the longitudinal axis of the plunger 2 by a bolt biasing member such as a compression spring 18.

Figure 4A:
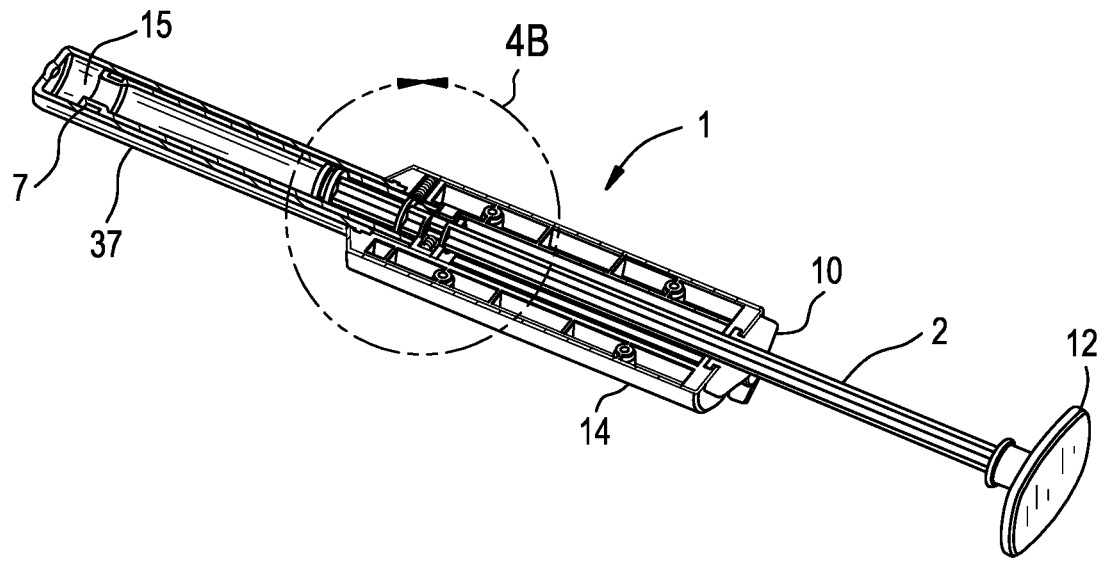
FIG. 4A is a partial cross-sectional view taken along plane 4A-4A of FIG. 3, that shows a locking slide assembly of the advanced inflation device, and shows the state of the locking slide assembly during which a plunger is locked to a large piston.
Figure 4B:
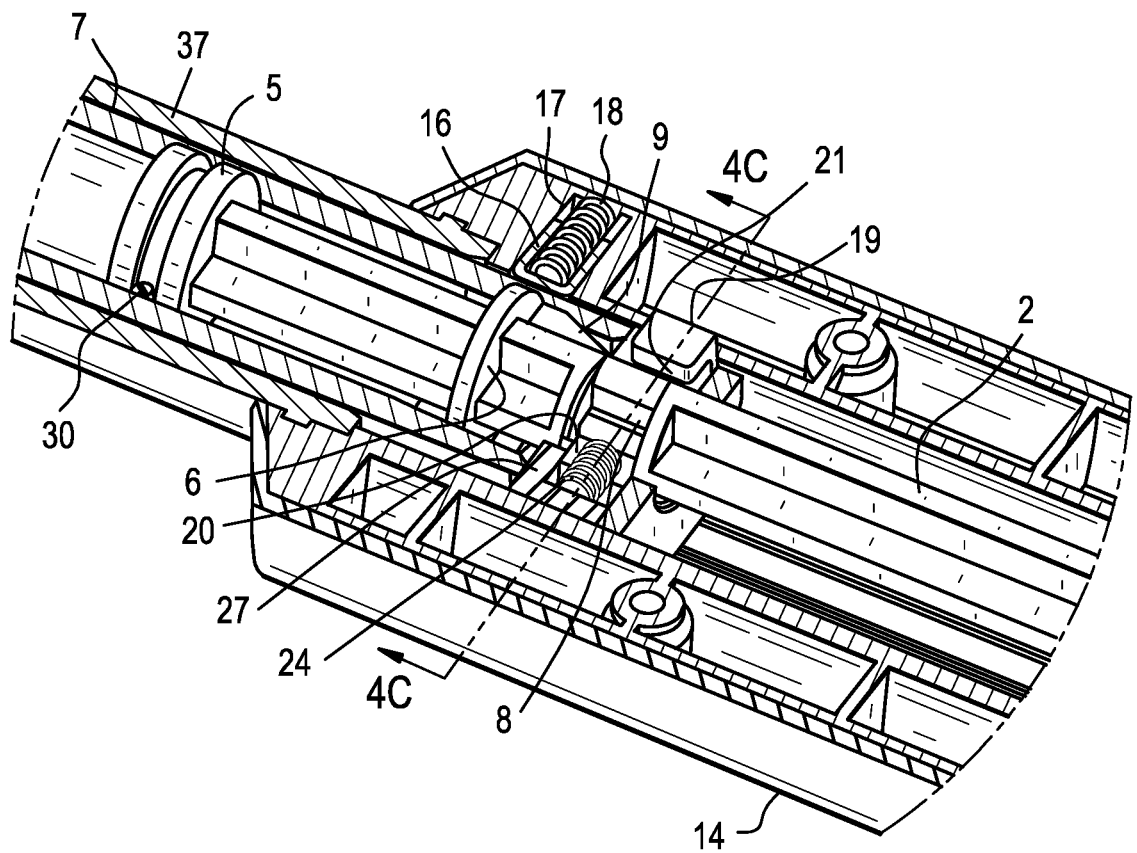
FIG. 4B is an enlarged view of a portion of FIG. 4A.
Figure 4C:
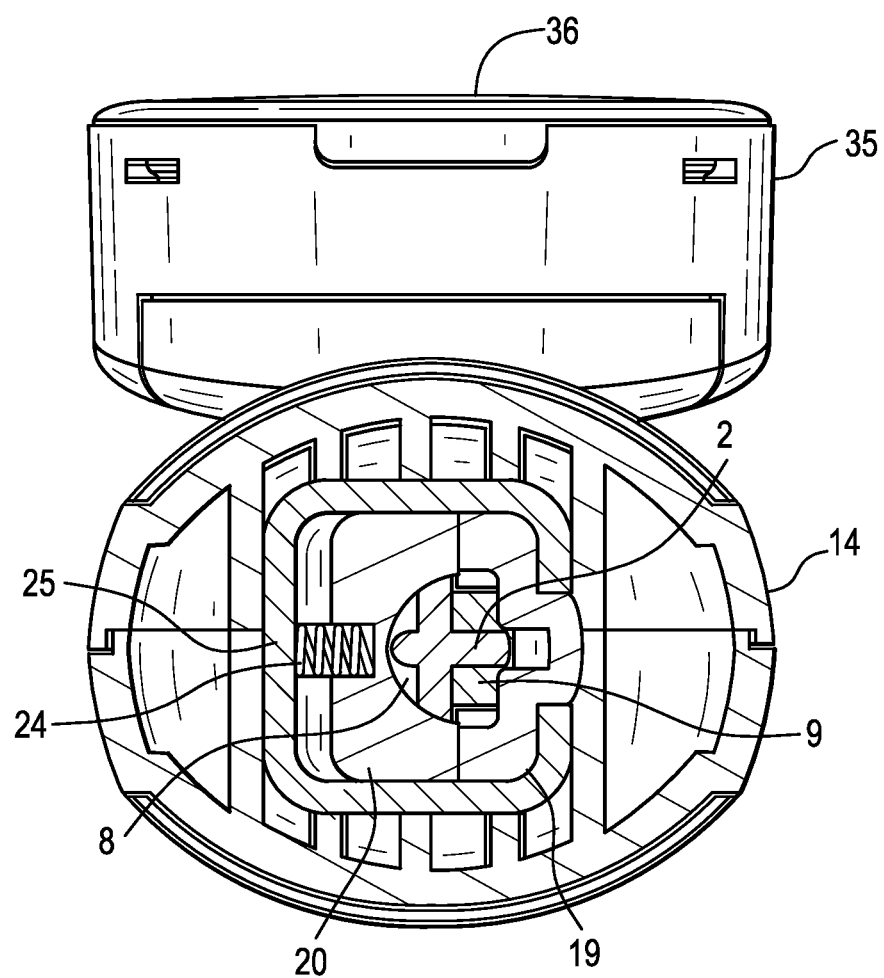
FIG. 4C is a cross-sectional view taken along line 4C-4C of FIG. 4B.

As shown in FIGS. 5A and 5B, when the handle 12 of the plunger 2 is pulled by a user such that the control plunger 2 is moved to a full proximal position, the large piston 7 is withdrawn proximally by its abutment against the piston shoulder 6 as it moves with the control plunger 2. On the other hand, once the control plunger 2 is moved distally from this full proximal condition, the plunger latch 20 aligns with the at least one plunger stop 8 of the control plunger 2 allowing it to be driven into engagement by the latch biasing member 24. This locking engagement of the control plunger 2 and the large piston 7 ties both pistons together and allows them to move distally as one in a synchronous manner as shown in FIGS. 4A, 4B and 4C, within the locking chamber 25 at the proximal end of the large piston 7.

Figure 6A:
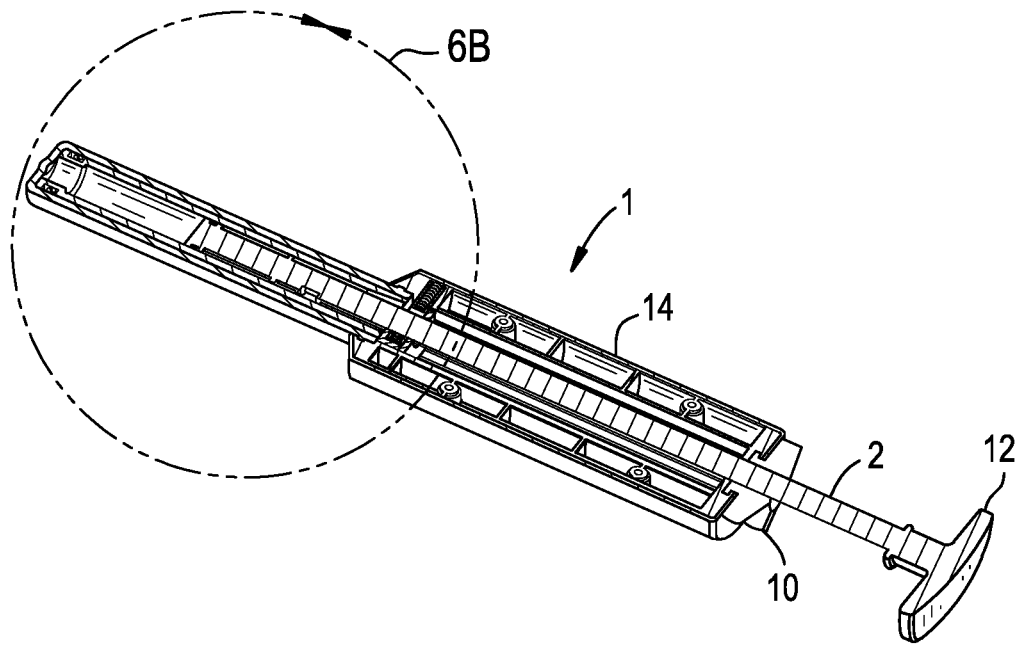
FIG. 6A is similar to FIG. 4A but shows a different state of the locking slide assembly, specifically a state during which the large piston is latched to a housing of the device by biased bolt and the plunger with small piston is in mid-travel.
Figure 8:
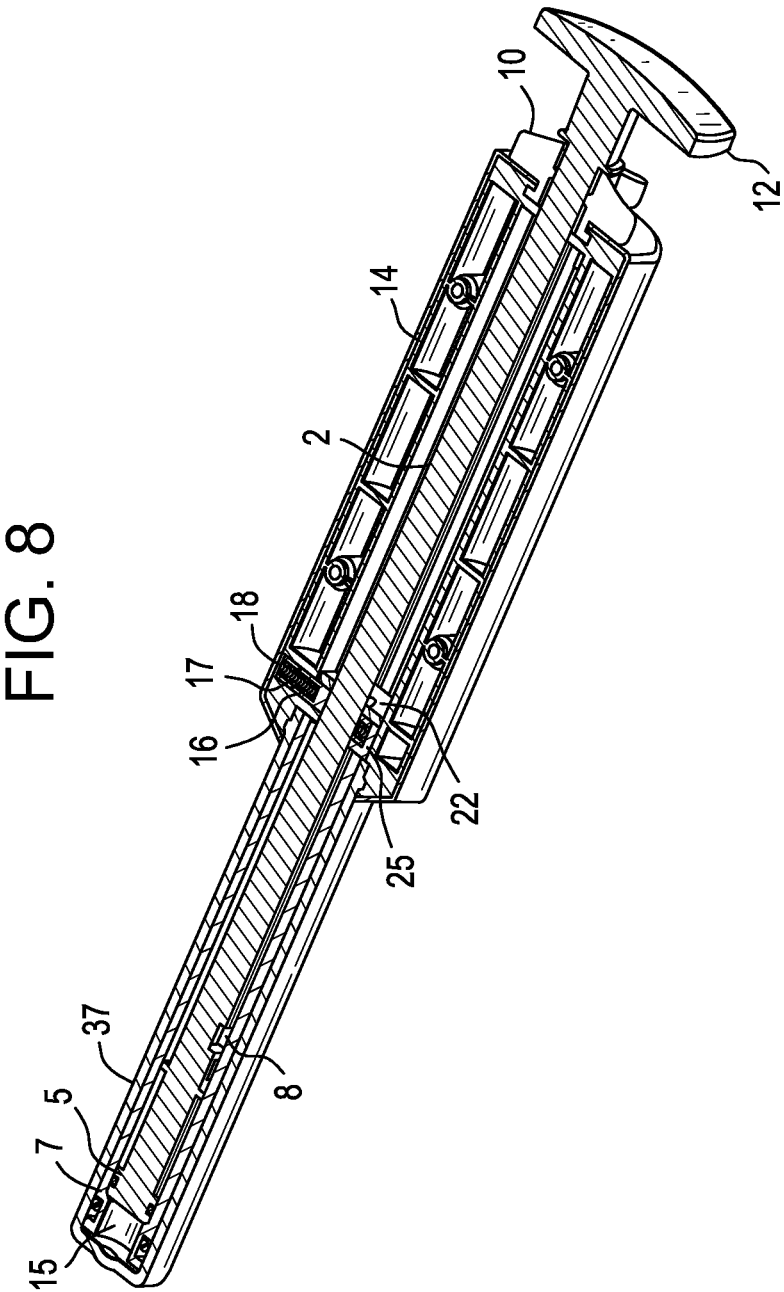
FIG. 8 is similar to FIG. 4A but shows the plunger unlocked from the large piston and in the fully distal, discharged position with the large piston locked to the housing of the device by the biased bolt.

As best seen in FIG. 6A, after the large piston 7 (with piston seal 29) reaches its full distal travel limit, thereby delivering, for example, approximately 50% to 80% of fluid fill required by the delivery balloon catheter 33, the large piston 7 becomes locked in place within the inflation device housing 14. The locking of the large piston 7 is performed by the biased bolt 16 and this causes the locking slide assembly 13 to release the plunger 2 and allow the small piston 5 to continue moving to its full distal position as shown in FIG. 8. In this manner, the small piston 5 is allowed to deliver the remaining 50% to 20% of fluid, for example, to complete expansion of the stent delivery balloon at reduced plunger force as illustrated by curve "B" of FIG. 1. All fluid displaceable within the inflation device fluid chamber 15 is thereby dispensed by the user's single continuous distal force upon the control plunger 2. Because this locking and unlocking action occurs automatically in response to the positions of the control plunger 2 and large piston 7, no secondary user input to effect locking or releasing is required and the locking and unlocking action between pistons is therefore transparent to the user.

Figure 7A:
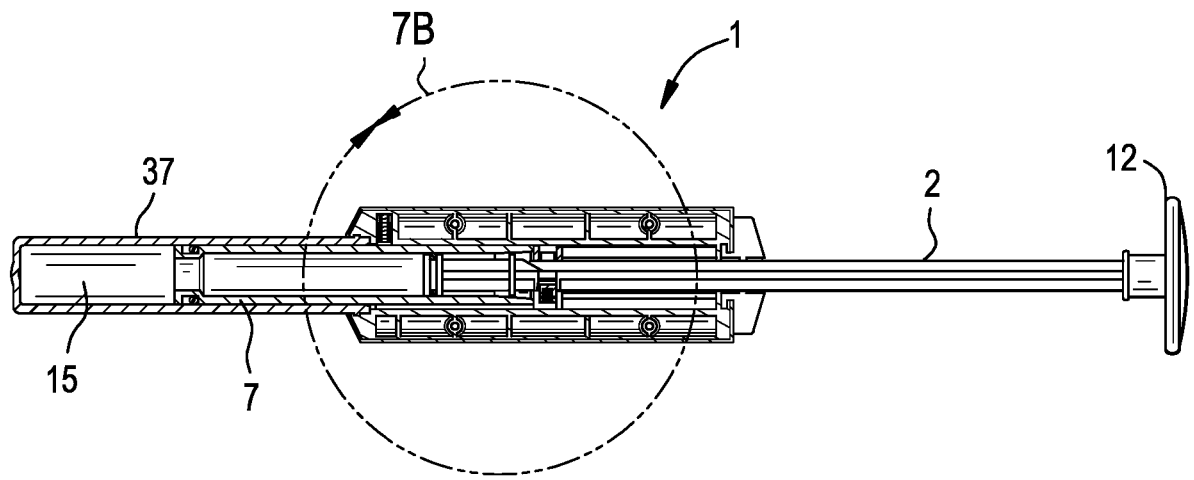
FIG. 7A is similar to FIG. 4A but shows a different state of the locking slide assembly, specifically a state during which the large piston is in mid-travel and locked to the plunger after being unlocked from the biased bolt.
Figure 7B:
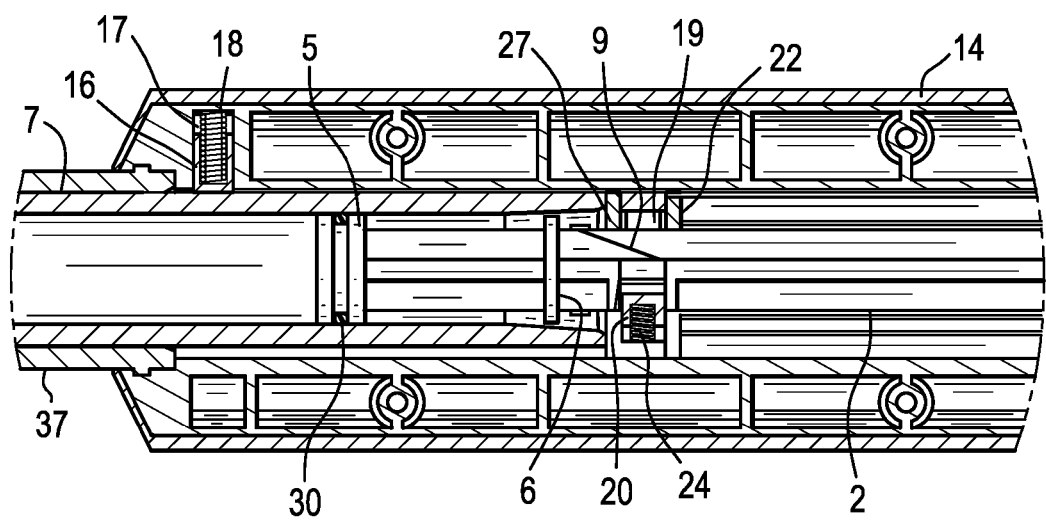
FIG. 7B is an enlarged view of a portion of FIG. 7A.

As shown in FIGS. 7A and 7B, the bolt 16 which controls automatic locking of the large piston 7 and its unlocking from the control plunger 2 is operable within a bolt guideway 17 and located at the proximal end of the bore 3 of the inflation device barrel 37. The bolt 16 within the bolt guideway 17 is urged toward the control plunger 2 by the bolt biasing member 18 which is also located within the bolt guideway 17. The bolt guideway 17 is oriented to allow the bolt 16 to be driven toward the central axis of the bore 3 of the inflation device barrel 37, therefore positioning the bolt 16 to act upon the actuator block 19 of the locking slide assembly 13 whenever the locking chamber 25 at the proximal end of large piston 7 aligns with it. As shown in FIGS. 4A and 4B, the bolt 16 is obstructed by an outer wall 26 of the large piston 7 and is only allowed to extend from the bolt guideway 17 after the outer piston wall 26 and a floor 27 of the locking chamber 25 move distally beyond it. Once no longer obstructed by the outer piston wall 26 and the locking chamber floor 27, the bolt 16 is free to extend over the locking chamber floor 27 and hold the piston 7 in its fully distal position. The bolt 16 residing within the bolt guideway 17 and aligned by it, can be either guided to traverse linearly as shown herein or alternatively be secured to the housing 14 and guided by a pivotable mounting as best suits space available within the device.

Figure 5C:
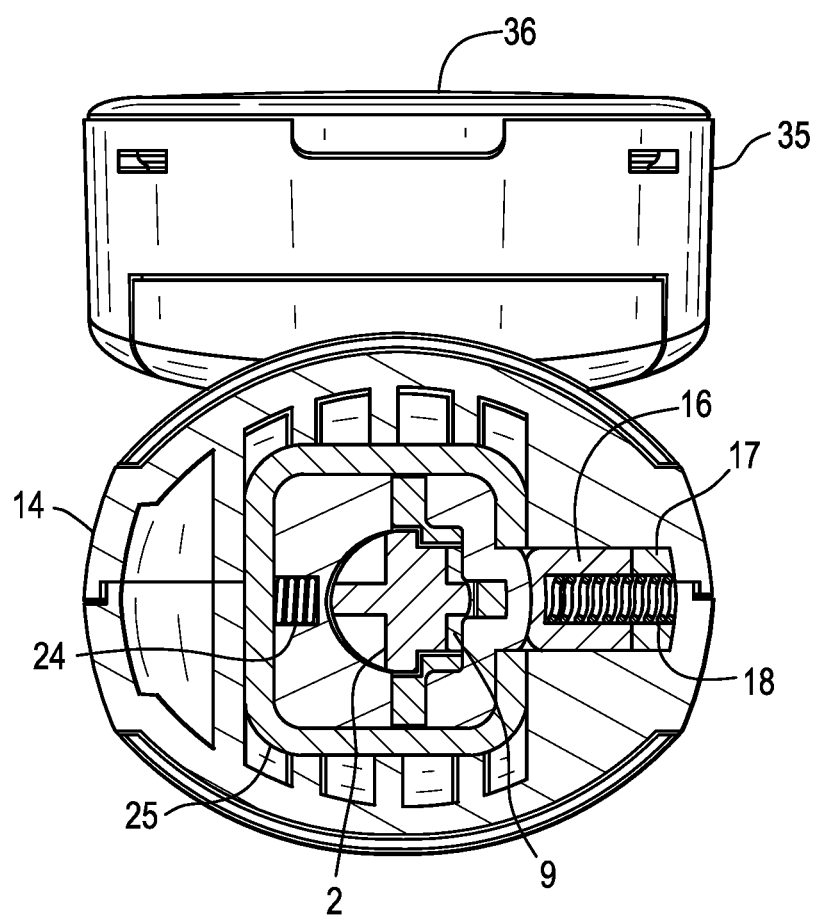
FIG. 5C is a cross-sectional view taken along line 5C-5C of FIG. 5B.

As mentioned previously, the locking slide assembly 13 preferably comprises plunger latch 20, actuator block 19 and a latch biasing member means 24. The plunger latch 20 is urged toward the plunger 2 by the biasing member 24 to engage the at least one plunger stop 8 of the control plunger 2. The plunger latch 20 and the actuator block 19 slidably engage one another as a result of surfaces 21 of the actuator block 19 engaging corresponding surfaces 23 of the plunger latch 20. The plunger latch 20 is lightly spring biased by the biasing member 24, to urge it toward the plunger 2. These abutting surfaces 21 and 23 allow the plunger latch 20 to be driven toward the control plunger 2 by the latch biasing member 24 whenever the actuator block 19 and the bolt 16 are moved away from the control plunger 2, preferably by a cam 9 that is provided on the piston shoulder 6, as shown in FIGS. 5A, 5B and 5C. Conversely, the abutting surfaces 21 and 23 allow the plunger latch 20 to be driven away from the control plunger 2 when the biasing member 18 of the bolt 16 overcomes the force of the biasing member 24 of the plunger latch 20 and pushes the actuator block 19 toward the control plunger 2.

Figure 6B:
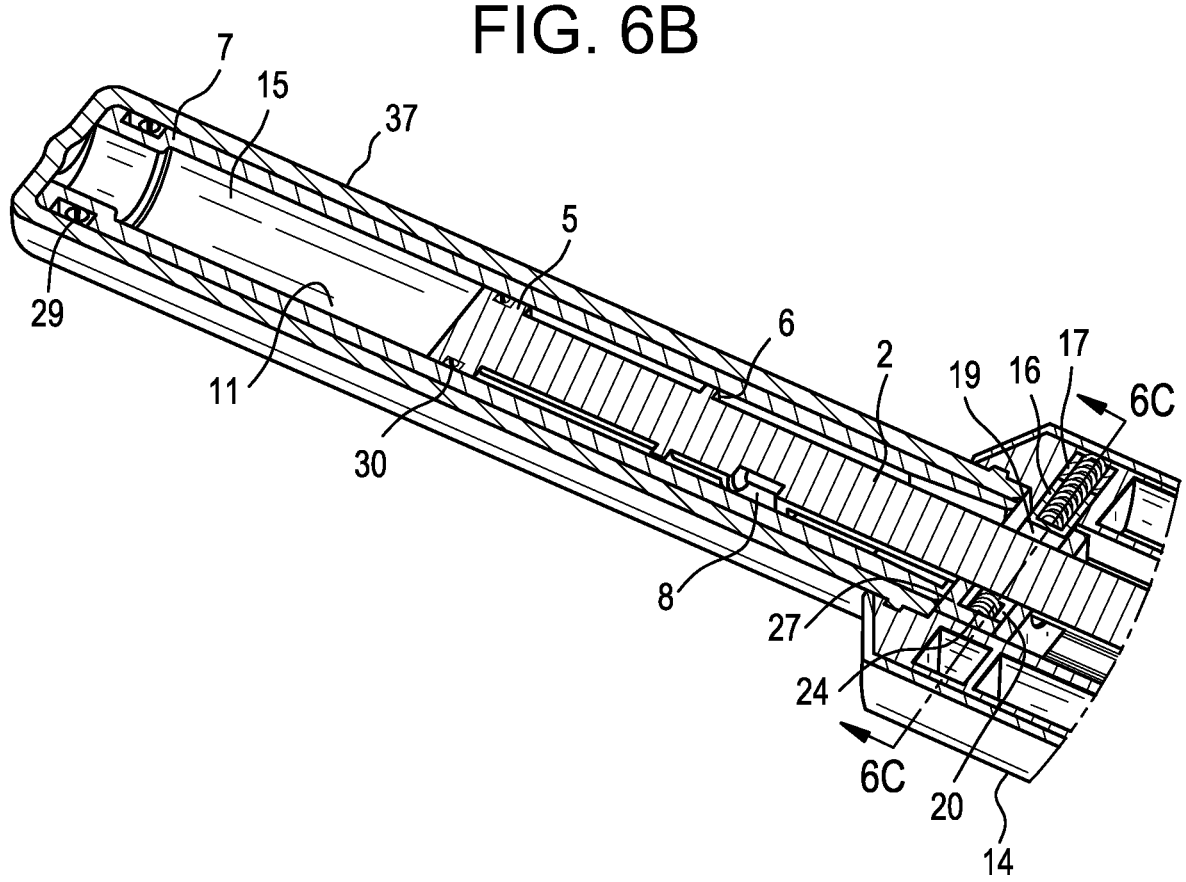
FIG. 6B is an enlarged view of a portion of FIG. 6A.
Figure 6C:
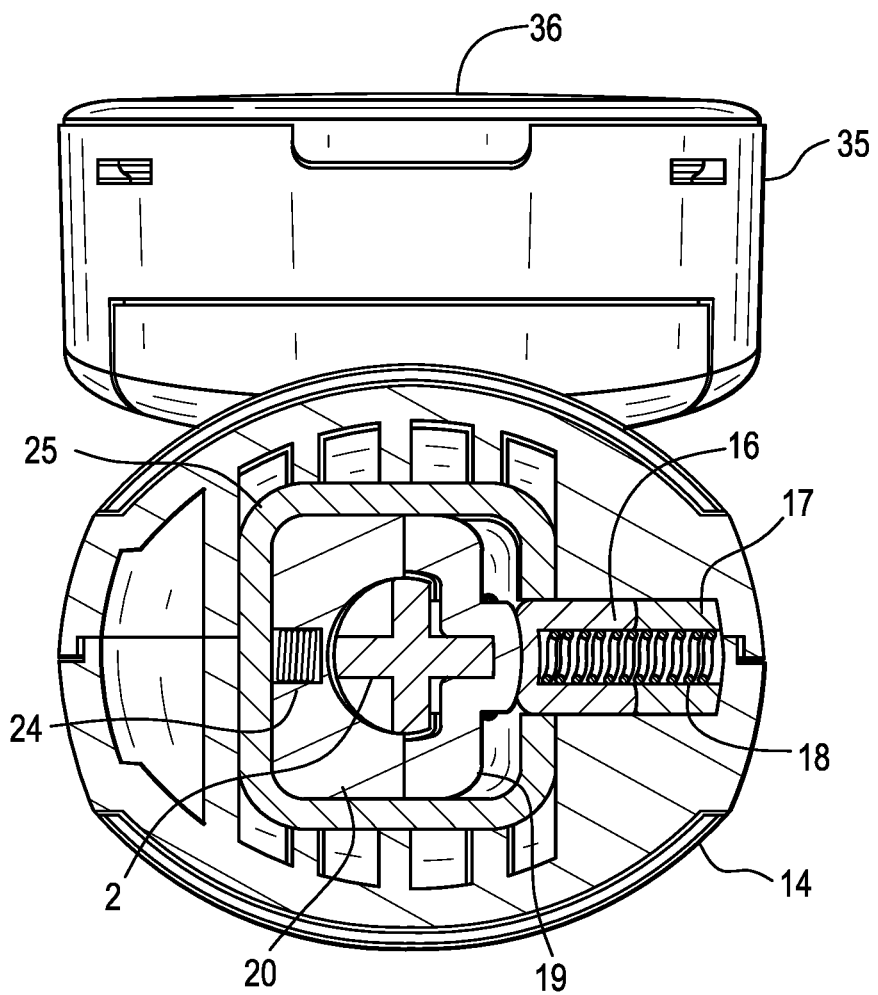
FIG. 6C is a cross-sectional view taken along line 6C-6C of FIG. 6B.

The locking slide assembly 13 always remains with the large piston 7 while the bolt 16 resides within the bolt guideway 17 at the proximal end of the bore 3 of the inflation device barrel 37. The bolt 16 is positioned within the bolt guideway 17 to be in alignment with the actuator block 19 of the locking slide assembly 13 whenever the large piston 7 reaches its distal most location. Therefore, whenever the large piston 7 reaches its distal most position, the bolt 16 becomes uncovered by the outer piston wall 26 and the locking chamber floor 27 and is therefore allowed to move toward the control plunger 2. This action of the bolt 16 locks the piston 7 in its distal most position as shown in FIGS. 6A and 6B, and drives the locking slide assembly 13 into an unlocked condition with the control plunger 2 as shown in FIG. 6C by compressing the latch biasing member 24 while releasing the plunger latch 20 from engagement with the at least one plunger stop 8 of the control plunger 2. This unlocking action releases the control plunger 2 from the large piston 7 in order to allow the small piston 5 to be freely driven distally as shown in FIGS. 6A and 6B to complete the displacement of the working fluid remaining within the fluid chamber 15. Therefore, the continuous distal movement of the control plunger 2 and movement of both pistons is controlled by an automatic locking and release mechanism that reacts to the location of the two fluid displacement pistons within the inflation device housing 14. The locking mechanism also retains the large piston 7 in a fully distal position within the bore 3 of the inflation device barrel 37 to prevent it from being hydraulically moved backward by pressure created during the continued advancement of the piston 5 within the fluid chamber 15.

Due to piston control from the locking assembly 13, advancement of the small piston 5 within the bore 11 of the large piston 7 to supply fluid through Luer bearing hose 4 to deliver an expandable prosthetic device 32 shown in FIG. 3, occurs during the highest delivery force demand period for expanding the delivery balloon 31. Deployment of the expandable prosthetic device 32 can therefore be accomplished with much less user force upon the handle 12 of the control plunger 2 than would be required if a single piston equal in diameter to the large piston 7 had been utilized. Because the effective area of the small piston 5 is less than that of the combined effective area of both pistons (5 and 7) advanced together, the amount of force required to advance the control plunger 2 during final balloon expansion is reduced by the percentage that the effective area of the large piston 7 represents of the combined effective area of both pistons (5 and 7).

After full advancement of the control plunger 2 and complete discharge of working fluid from the fluid chamber 15 by both pistons during a stent balloon inflation or alternatively, when initially filling the fluid chamber 15 with fluid from a fully discharged position of both pistons, withdrawing the control plunger 2 proximally, first moves the small piston 5 proximally. As the small piston 5 approaches its proximal limit of travel within the bore 11 of the piston 7, the cam 9 on the piston shoulder 6 engages the actuator block 19 and pushes it away from the control plunger 2 while the control plunger 2 continues to be withdrawn proximally toward the user. This movement of the actuator block 19 simultaneously pushes the bolt 16 in a direction away from the control plunger 2 and out of locking engagement with the large piston 7 thereby releasing piston 7 to be free to move proximally. As the large piston 7 moves proximally under operator force upon the control plunger 2, the outer wall 26 of the piston 7 blocks the bolt 16 from moving toward the center of control plunger 2. Both the small piston 5 and the large piston 7 are then able to operate again as one large surface area entity once piston shoulder 6 abuts the locking chamber floor 27. Both pistons therefore move as a set with the control plunger 2, back to the proximal travel limit of the large piston 7. By this sequence of events, working fluid is first drawn by small piston 5 into the small bore 11 within the large piston 7 followed by loading of the working fluid into the fluid chamber 15 within the bore 3 of the inflation device barrel 37 as the control plunger 2 continues to be withdrawn. As shown in FIG. 9, this action and sequence of events serves to evacuate working fluid from an expanded delivery balloon 31 into the fluid chamber 15 when both pistons are moved proximally.

The very same action and sequence of events that evacuates working fluid from the delivery balloon 31 also facilitates the initial filling of working fluid into the fluid chamber 15 when the advanced inflation device 1 is being prepared for use. Beginning with both the large piston 7 and the small piston 5 in their distal most positions, the large piston 7 is locked to the inflation device housing 14 by the bolt 16 while the small piston 5 is free to be moved by the plunger 2. Withdrawing the plunger 2 proximally first retracts the small piston 5 proximally until the small piston 5 has reached its most proximal position within the bore 11 of the piston 7 thereby allowing it to fill first with working fluid through the Luer bearing hose 4 before the piston shoulder 6 engages at the locking chamber floor 27 of the large piston 7. Further, as the small piston 5 approaches its most proximal position within the bore 11 of the piston 7, the actuator block 19, controlled by the cam 9 on the piston shoulder 6, drives the bolt 16 to release the large piston 7 allowing it to be withdrawn to its most proximal position to secondarily fill the remainder of the fluid chamber 15 with working fluid. The choreographed actions of the small piston 5 and the large piston 7 relative to one another (and controlled by the locking slide assembly 13) serves to allow sequential filling of their respective bores (11 and 3, respectively) as working fluid is drawn into the fluid chamber 15 through the Luer bearing hose 4 of the device 1. By this action, both the bore 11 of the piston 7 and the bore 3 of the inflation device barrel 37 are allowed to fill the fluid chamber 15 in order of their size, thereby minimizing the trapping of air within their respective bores and facilitating easy purging of any air bubbles that may become lodged within these bores.

With both pistons 5 and 7 at their proximal most position as shown in FIG. 9, purging of any entrained air or working fluid from the fluid chamber 15 can be accomplished by pressing the fully extended plunger 2 distally to drive both the small piston 5 and the large piston 7 distally, the small piston 5 remaining locked inside the bore 11 within the large piston 7 by plunger latch 20. Once the large piston 7 reaches its distal most position within the bore of the barrel 37, it is locked to the housing 14 by the bolt 16. Immediately upon the large piston 7 being locked against further movement, the small piston 5 is unlocked from the large piston 7 to continue travelling distally as the plunger 2 moves fully distal as shown in FIG. 8. Entrained air of working fluid contained within the device 1 is thereby discharged through the Luer bearing hose 4.

During the filling of a delivery balloon 31 to set an expandable prosthetic device 33, the first stages of fill depicted by segment "1" of curve "A" in FIG. 1, is accomplished through rapid distal advancement of the large piston 7 containing the small piston 5. This advancement of both pistons 5 and 7 (controlled by user force applied to the handle 12 of the control plunger 2) rapidly displaces a large amount of fluid at a relatively low plunger force as shown, in order to quickly accomplish the initial large volume filling of the delivery balloon 31. A piston having the combined swept areas of both large piston 7 and small piston 5 would require a substantial plunger force to continue filling the delivery balloon 31 as shown by segment "2" of curve "A" in FIG. 1 were it not for the unlocking of small piston 5.

Unlocking the small piston 5 to complete filling of the delivery balloon 31 provides for a significant reduction of the plunger force necessary to complete the filling of delivery balloon 31 during final setting of an expandable prosthetic device 32, as shown by curve "B" of FIG. 1. As can be seen, the user force upon the plunger 2 of the device 1 necessary to rapidly complete balloon expansion for delivery of the expandable prosthetic device 32 is thereby reduced to a more user manageable level by introduction of the smaller piston 5.

The respective diameters and fluid displacement volumes of both the large piston 7 and the small piston 5 can be widely adjusted to tailor their plunger force demand properties to best suit the inflation characteristics of a given delivery balloon 31 and its respective expandable prosthetic device 32.

In essence, the bolt 16 and associated biasing member 18 can collectively be thought to be a first locking mechanism (i.e., a locking mechanism that locks and unlocks the piston 7 relative to the housing 14), and the locking slide assembly 13 can be collectively thought to be a second locking mechanism (i.e., a locking mechanism that locks and unlocks the plunger 2 relative to the piston 7). As such, the first locking mechanism (i.e., the bolt 16 and associated biasing member 18) is not only a locking mechanism but, due to how the device 1 is configured to operate, is also an actuating mechanism with regard to actuating the second locking mechanism (i.e., the locking slide assembly 13) from a locked to an unlocked state. In other words, when the first locking mechanism (i.e., bolt 16) locks, the first locking mechanism also unlocks the second locking mechanism. When the piston 7 locks in place in the housing 14, the plunger 2 gets unlocked from the piston 7. As such, piston 7 is either generally locked to the housing 14 or locked to the plunger 2, depending on the state of operation of the device 1 (i.e., depending on the extent to which the handle 12 has been pushed into or pulled out of the housing 14). Therefore, the first and second locking mechanisms collectively can be thought of as being a single actuator that works to selectively lock the piston 7 to either the housing 14 or the plunger 2.

It should be understood that in no instance is any piston ever required or caused to move in response to hydraulic pressure within the fluid chamber 15 in a direction of travel opposite to that of the user driven control plunger 2 in order to facilitate orchestration of automatic locking or unlocking actions within the device 1. During the filling phase of a delivery balloon's expansion, fluid displacement from the fluid chamber 15 is always maintained and never momentarily interrupted or absorbed by the action of any piston or valve nor is any user input upon the control plunger 2 motion lost, in order to facilitate the operation of this device. Any depressurization of the fluid chamber 15 must be initiated by the user's intentional change of force against the control plunger 2. Further, operation of the switching mechanism that controls the movement of either piston within the advanced inflation device 1 is strictly dependent upon the location of the large piston 7 and small piston 5 relative to the bore 3 of the inflation device barrel 37. In order to assure predictability and performance consistency of the device 1, the locking slide assembly 13 that synchronizes piston movements is designed to operate without need for or reliance upon any hydraulic pressure dependent or, mechanically actuated valving means or, elastic deflection of components responding to hydraulic pressure or, frictional engagement of detenting mechanisms.

While a specific embodiment of the invention has been shown and described, it is envisioned that those skilled in the art may devise various modifications without departing from the spirit and scope of the present invention.

What is claimed is:

1. A fluid displacement and pressurizing device comprising: a housing; a first piston in the housing; a plunger which extends from the housing and has a second piston thereon; and an actuator which, when the second piston is in a first position within the fluid displacement and pressuring device, locks the first piston to the housing, and when the second piston is in a second position within the fluid displacement and pressuring device, locks the first piston to the plunger, wherein the first piston is locked to the housing when the second piston is in the first position within the fluid displacement and pressuring device and wherein the first piston is locked to the plunger when the second piston is in the second position within the fluid displacement and pressuring device.

2. A fluid displacement and pressurizing device as recited in claim 1, wherein the actuator comprises a first locking mechanism that locks and unlocks the first piston relative to the housing and a second locking mechanism that locks and unlocks the plunger relative to the first piston.

3. A fluid displacement and pressurizing device as recited in claim 2, wherein the first locking mechanism comprises an actuating mechanism with regard to actuating the second locking mechanism.

4. A fluid displacement and pressurizing device as recited in claim 1, further comprising a holding mechanism on the housing configured to selectively lock and unlock the plunger in place relative to the housing.

5. A fluid displacement and pressurizing device as recited in claim 1, wherein the plunger is thread-less.

6. A fluid displacement and pressurizing device as recited in claim 1, further comprising a barrel having a bore, wherein the first piston comprises a bore, wherein the plunger has a handle thereon, said handle being at an end of the plunger which is opposite the second piston that is on the plunger, wherein a first piston seal is provided on the first piston and a second piston seal is provided on the second piston, wherein the first piston seal seals with the bore of the barrel, wherein the second piston seal seals with the bore of the first piston, wherein the second piston slides back and forth in the bore of the first piston, and wherein the first piston slides back and forth in the bore of the barrel.

7. A fluid displacement and pressurizing device as recited in claim 6, wherein the actuator comprises a locking slide assembly comprising a plunger latch, a latch biasing member, and an actuator block.

8. A fluid displacement and pressurizing device as recited in claim 7, wherein the plunger provides a piston shoulder and at least one plunger stop, wherein there is a bolt inside the housing that is driven toward a longitudinal axis of the plunger by a bolt biasing member.

9. A fluid displacement and pressurizing device as recited in claim 8, wherein when the handle of the plunger is pulled by a user such that the plunger is moved to a full proximal position, the first piston is withdrawn proximally by its abutment against the piston shoulder provided by the plunger, wherein once the plunger is moved distally from the full proximal condition, the plunger latch aligns with the at least one plunger stop of the plunger allowing the plunger latch to be driven into engagement by the latch biasing member, wherein the locking engagement of the plunger and the first piston ties both first and second pistons together and allows them to move distally as one in a synchronous manner.

10. A fluid displacement and pressurizing device as recited in claim 9, wherein when the first piston reaches its full distal travel limit, the first piston becomes locked in place within the housing, wherein the locking of the first piston is performed by the bolt and this causes the locking slide assembly to release the plunger and allow the second piston to continue moving to its full distal position.

11. A fluid displacement and pressurizing device as recited in claim 10, wherein the bolt controls automatic locking of the first piston and its unlocking from the plunger is operable within a bolt guideway and located at the proximal end of the bore of the barrel, wherein the bolt within the bolt guideway is urged toward the plunger by the bolt biasing member which is also located within the bolt guideway, wherein the bolt guideway is oriented to allow the bolt to be driven toward a central axis of the bore of the barrel, therefore positioning the bolt to act upon the actuator block of the locking slide assembly whenever the locking chamber at the proximal end of first piston aligns with the bolt.

12. A fluid displacement and pressurizing device as recited in claim 11, wherein the bolt is obstructed by an outer wall of the first piston and is only allowed to extend from the bolt guideway after an outer piston wall and a floor of the locking chamber move distally beyond the bolt, wherein once the bolt is no longer obstructed by the outer piston wall and the floor of the locking chamber, the bolt is free to extend over the floor of the locking chamber and hold the piston in its fully distal position.

13. A fluid displacement and pressurizing device as recited in claim 7, wherein the plunger latch is urged toward the plunger by the latch biasing member to engage the at least one plunger stop of the plunger.

14. A fluid displacement and pressurizing device as recited in claim 13, wherein the plunger latch and the actuator block slidably engage one another as a result of surfaces of the actuator block engaging corresponding surfaces of the plunger latch, wherein the plunger latch is biased by the latch biasing member to urge the plunger latch toward the plunger.

15. A fluid displacement and pressurizing device as recited in claim 14, wherein the plunger latch is driven toward the plunger by the latch biasing member whenever the actuator block and the bolt are moved away from the plunger.

16. A fluid displacement and pressurizing device as recited in claim 15, wherein the plunger provides a piston shoulder and at least one plunger stop, wherein there is a bolt inside the housing that is driven toward a longitudinal axis of the plunger by a bolt biasing member, wherein a cam is provided on the piston shoulder and the cam moves the actuator block and the bolt away from the plunger.

17. A fluid displacement and pressurizing device comprising: a housing; a first piston in the housing; a plunger which extends from the housing and has a second piston thereon; and an actuator which selectively locks the first piston the housing or the plunger depending on a position of the second piston within the fluid displacement and pressurizing device, further comprising a barrel having a bore, wherein the first piston comprises a bore, wherein the plunger has a handle thereon, said handle being at an end of the plunger which is opposite the second piston that is on the plunger, wherein a first piston seal is provided on the first piston and a second piston seal is provided on the second piston, wherein the first piston seal seals with the bore of the barrel, wherein the second piston seal seals with the bore of the first piston, wherein the second piston slides back and forth in the bore of the first piston, and wherein the first piston slides back and forth in the bore of the barrel, wherein the actuator comprises a locking slide assembly comprising a plunger latch, a latch biasing member, and an actuator block, wherein the plunger provides a piston shoulder and at least one plunger stop, wherein there is a bolt inside the housing that is driven toward a longitudinal axis of the plunger by a bolt biasing member.

18. A fluid displacement and pressurizing device as recited in claim 17, wherein when the handle of the plunger is pulled by a user such that the plunger is moved to a full proximal position, the first piston is withdrawn proximally by its abutment against the piston shoulder provided by the plunger, wherein once the plunger is moved distally from the full proximal condition, the plunger latch aligns with the at least one plunger stop of the plunger allowing the plunger latch to be driven into engagement by the latch biasing member, wherein the locking engagement of the plunger and the first piston ties both first and second pistons together and allows them to move distally as one in a synchronous manner.

19. A fluid displacement and pressurizing device as recited in claim 18, wherein when the first piston reaches its full distal travel limit, the first piston becomes locked in place within the housing, wherein the locking of the first piston is performed by the bolt and this causes the locking slide assembly to release the plunger and allow the second piston to continue moving to its full distal position.

20. A fluid displacement and pressurizing device as recited in claim 19, wherein the bolt controls automatic locking of the first piston and its unlocking from the plunger is operable within a bolt guideway and located at the proximal end of the bore of the barrel, wherein the bolt within the bolt guideway is urged toward the plunger by the bolt biasing member which is also located within the bolt guideway, wherein the bolt guideway is oriented to allow the bolt to be driven toward a central axis of the bore of the barrel, therefore positioning the bolt to act upon the actuator block of the locking slide assembly whenever the locking chamber at the proximal end of first piston aligns with the bolt.

21. A fluid displacement and pressurizing device as recited in claim 20, wherein the bolt is obstructed by an outer wall of the first piston and is only allowed to extend from the bolt guideway after an outer piston wall and a floor of the locking chamber move distally beyond the bolt, wherein once the bolt is no longer obstructed by the outer piston wall and the floor of the locking chamber, the bolt is free to extend over the floor of the locking chamber and hold the piston in its fully distal position.

* * * * *